(12) United States Patent  
Puri

(10) Patent No.: US 11,919,859 B2
(45) Date of Patent: Mar. 5, 2024

(54) HERBICIDAL MIXTURE, COMPOSITION AND METHOD

(71) Applicant: FMC Corporation, Philadelphia, PA (US)

(72) Inventor: Atul Puri, Wilmington, DE (US)

(73) Assignee: FMC Corporation, Philadelphia, PA (US)

( * ) Notice: Subject to any disclaimer, the term of this patent is extended or adjusted under 35 U.S.C. 154(b) by 88 days.

(21) Appl. No.: 16/495,724

(22) PCT Filed: Mar. 16, 2018

(86) PCT No.: PCT/US2018/022849
§ 371 (c)(1),
(2) Date: Sep. 19, 2019

(87) PCT Pub. No.: WO2018/175231
PCT Pub. Date: Sep. 27, 2018

(65) Prior Publication Data
US 2020/0095202 A1 Mar. 26, 2020

Related U.S. Application Data

(60) Provisional application No. 62/572,057, filed on Oct. 13, 2017, provisional application No. 62/474,215, filed on Mar. 21, 2017.

(51) Int. Cl.
| | |
|---|---|
| *C07D 213/79* | (2006.01) |
| *A01N 25/02* | (2006.01) |
| *A01N 25/08* | (2006.01) |
| *A01N 43/36* | (2006.01) |
| *A01N 43/40* | (2006.01) |
| *C07D 207/277* | (2006.01) |
| *C07D 401/04* | (2006.01) |
| *C07D 401/12* | (2006.01) |

(52) U.S. Cl.
CPC ........... *C07D 213/79* (2013.01); *A01N 25/02* (2013.01); *A01N 25/08* (2013.01); *A01N 43/36* (2013.01); *A01N 43/40* (2013.01); *C07D 207/277* (2013.01); *C07D 401/04* (2013.01); *C07D 401/12* (2013.01)

(58) Field of Classification Search
CPC .............. C07D 213/79; C07D 207/277; C07D 401/04; C07D 401/12; A01N 25/02; A01N 25/08; A01N 43/36; A01N 43/40
See application file for complete search history.

(56) References Cited

U.S. PATENT DOCUMENTS

| | | |
|---|---|---|
| 3,741,989 A | 6/1973 | Zaugg |
| 3,959,481 A | 5/1976 | Davis et al. |
| 4,594,094 A | 6/1986 | Kollmeyer |
| 4,874,422 A | 10/1989 | Woolard |
| 5,196,534 A | 3/1993 | Whitehead et al. |
| 5,856,273 A | 1/1999 | Kay et al. |
| 7,205,318 B2 | 4/2007 | Qiao et al. |
| 7,355,053 B2 | 4/2008 | Reinhard et al. |
| 7,375,232 B2 | 5/2008 | Clark et al. |
| 8,293,926 B2 | 10/2012 | Yasuoka et al. |
| 8,461,202 B2 | 6/2013 | Sancho Sanz et al. |
| 8,575,154 B2 | 11/2013 | Kori et al. |
| 8,946,216 B2 | 2/2015 | Deng et al. |
| 9,119,397 B2 | 9/2015 | Yerkes et al. |

(Continued)

FOREIGN PATENT DOCUMENTS

| | | |
|---|---|---|
| CN | 102531918 | 10/2013 |
| CN | 106106456 | 11/2016 |

(Continued)

OTHER PUBLICATIONS

Campaigne et el.; Synthesis of Some Ureidodihydrofurans and Related Pyrimidones as Potential Antimalarials; J. Med. Chem .; 1969; 339-342. (XP002278920).

(Continued)

*Primary Examiner* — Erin E Hirt
(74) *Attorney, Agent, or Firm* — Reed A Coats; FMC Corporation

(57) ABSTRACT

Disclosed is a mixture comprising (a) a compound of Formula I and salts thereof wherein $A^1$, $A^2$, $A^3$, $R^1$, $B^1$, $B^2$ and $B^3$ are defined in the disclosure, and (b) 2-pyridinecarboxylic acid, 4-amino-3-chloro-6-(4-chloro-2-fluoro-3-methoxyphenyl)-5-fluoro-, phenylmethyl ester (i.e. florpyrauxifen-benzyl). Also disclosed is a composition comprising the mixture. Also disclosed is a method of applying the mixture to undesired vegetation comprising contacting the undesired vegetation or its environment with an effective amount of the mixture of the invention.

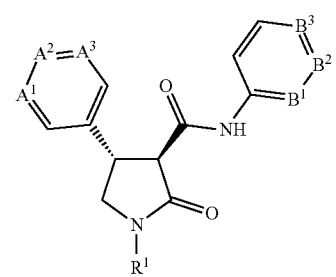

I

8 Claims, No Drawings

(56) References Cited

U.S. PATENT DOCUMENTS

| | | | |
|---|---|---|---|
| 9,446,995 | B2 | 9/2016 | Chong |
| 9,737,073 | B2 | 8/2017 | Gifford et al. |
| 9,944,602 | B2 | 4/2018 | Satterfield et al. |
| 9,969,728 | B2 | 5/2018 | Defays et al. |
| 10,227,286 | B2 | 3/2019 | Satterfield |
| 10,294,202 | B2 | 5/2019 | Satterfield et al. |
| 10,405,547 | B2 | 9/2019 | Satterfield et al. |
| 10,442,807 | B2 | 10/2019 | Campbell et al. |
| 10,654,804 | B2 | 5/2020 | Satterfield et al. |
| 10,875,838 | B2 | 12/2020 | Chen et al. |
| 11,178,873 | B2 | 11/2021 | Satterfield et al. |
| 2004/0242671 | A1 | 12/2004 | Grimee et al. |
| 2007/0123508 | A1 | 5/2007 | Olsson et al. |
| 2009/0062366 | A1 | 3/2009 | Hachiya et al. |
| 2009/0203694 | A1 | 8/2009 | Hurley et al. |
| 2010/0137137 | A1 | 6/2010 | Rosinger et al. |
| 2011/0218199 | A1 | 9/2011 | Georges et al. |
| 2012/0115737 | A1 | 5/2012 | Ehrich et al. |
| 2014/0031220 | A1 | 1/2014 | Yerkes et al. |
| 2014/0031224 | A1* | 1/2014 | Yerkes ............... A01N 43/40 504/105 |
| 2015/0173371 | A1 | 6/2015 | Mann et al. |
| 2016/0137639 | A1 | 5/2016 | Kotoku et al. |
| 2018/0049437 | A1 | 2/2018 | Satterfield et al. |
| 2018/0057442 | A1 | 3/2018 | Satterfield |
| 2018/0077931 | A1 | 3/2018 | Stevenson et al. |
| 2018/0099935 | A1 | 4/2018 | Satterfield et al. |
| 2018/0141904 | A1 | 5/2018 | Campbell et al. |
| 2018/0213788 | A1 | 8/2018 | Satterfield et al. |
| 2020/0115337 | A1 | 4/2020 | Campbell |
| 2020/0154709 | A1 | 5/2020 | McMahon |

FOREIGN PATENT DOCUMENTS

| | | |
|---|---|---|
| DE | 1262277 | 3/1968 |
| EP | 2336104 | 6/2011 |
| IN | 146DEL08 | 6/2008 |
| JP | 51131870 | 11/1976 |
| JP | 52156859 | 12/1977 |
| JP | 53-056288 | 5/1978 |
| JP | 54-088114 | 7/1979 |
| JP | H0770037 | 3/1995 |
| JP | 08-269145 | 10/1996 |
| JP | 2018104419 | 7/2018 |
| KR | 20130142477 | 12/2013 |
| RU | 2555370 | 7/2015 |
| WO | 200009481 | 2/2000 |
| WO | 2002/006512 | 1/2002 |
| WO | 2004046081 | 6/2004 |
| WO | 2006081562 | 8/2006 |
| WO | 2006/127396 | 11/2006 |
| WO | 2009/029518 | 3/2009 |
| WO | 2009062371 | 5/2009 |
| WO | 2010/099279 | 9/2010 |
| WO | 2011/103225 | 8/2011 |
| WO | 20120034957 | 3/2012 |
| WO | 2013/014165 | 1/2013 |
| WO | 2014/018359 | 1/2014 |
| WO | 2015084796 | 6/2015 |
| WO | 2016003997 | 1/2016 |
| WO | 2016094117 | 6/2016 |
| WO | 2016164201 | 10/2016 |
| WO | 2016176082 | 11/2016 |
| WO | 2016182780 | 11/2016 |
| WO | 2016196019 | 12/2016 |
| WO | 2016196593 | 12/2016 |
| WO | 20170023515 | 2/2017 |
| WO | 2017/075559 | 5/2017 |
| WO | 2018/065311 | 4/2018 |
| WO | 20180118384 | 6/2018 |
| WO | 201801752226 | 9/2018 |
| WO | 2018222646 | 12/2018 |
| WO | 2018222647 | 12/2018 |

OTHER PUBLICATIONS

Cauliez et al.; "Studies on Pyrrolidinones. On the Carbamoylation of Some Pyroglutamic Derivatives"; J. Het. Chem.; 33; 1996; 1233-1237. (XP055297107).

Hwang et al.; "Diastereoselective Synthesis of Oxazolidinone Derivatives and Their Antifungal Activities"; Korean J. of Med. Chem.; vol. 4, No. 1; 1994; 52-56. (XP009191451).

IPCOM000241978D; Jun. 11, 2015.

PubChem Entry CID 29937915 (4S)-4-[3-(trifluoromethyl)phenyl]pyrrolidin-2-one: May 28, 2009.

XP002734980; Jan. 20, 2002.

XP002734981; WO0009481; Feb. 24, 2000.

XP002759805; Jan. 20, 2002.

XP002759806; Mar. 23, 2009.

Murata et al.; "Oxidation of N-Acyl-Pyrrolidines and -Piperidines with Iron(II)-Hydrogen Peroxide and an Iron Complex-Molecular Oxygen"; J. Chem. Soc. Perkin Trans.; 1987; 1259-1262. (XP055297105).

International Search Report of corresponding PCT/US2018/022849 dated May 30, 2018.

Banerjee et al., "A Stereoselective Cyclization Strategy for the Preparation of gamma-Lactams and Their Use in the Synthesis of alpha-Methyl-beta-Proline", J. Org. Chem. 2012, vol. 77, p. 10925-10930.

Wang et al., "Asymmetric Cyanation of Activated Olefins with Ethyl Cyanoformate Catalyzed by a Modular Titanium Catalyst", Org. Lett., 2010, vol. 12(6), pp. 1280-1283.

Hajra et al., "Organocatalytic enantioselective conjugate addition of nitromethane to alkylidenemalonates: asymmetric synthesis of pyrrolidine-3-carboxylic acid derivatives", RSC Advances, vol. 3, No. 26, Jan. 1, 2013, pp. 10185-10188 (XP055665141).

CN Decision, "Invalidation Request Examination Decision," in CN Appln. No. 201480074726.8, dated Apr. 20, 2021, 23 pages.

CN Opposition, "Request for Invalidation of a Patent Right," in CN Appln. No. 201480074726.8, dated Sep. 9, 2020, 49 pages (English Translation).

CN Support, "Declaration of Aman Chandi," in CN Appln. No. 201480074726.8, dated Dec. 18, 2020, 9 pages.

CN Support, "Declaration of Steven Gutteridge," in CN Appln. No. 201480074726.8, dated Dec. 18, 2020, 5 pages.

CN Support, "Declaration of Steven Gutteridge," in CN Appln. No. 201480074726.8, dated Feb. 10, 2021, 5 pages.

EP Opposition Response, "Auxiliary Request 1—marked up," in EP Appln No. 14815174.9, from response dated Jun. 25, 2021, 10 pages.

EP Opposition Response, "Auxiliary Request 1," in EP Appln No. 14815174.9, from response dated Jun. 25, 2021, 10 pages.

EP Opposition Response, "Auxiliary Request 2—marked up," in EP Appln No. 14815174.9, from response dated Jun. 25, 2021, 10 pages.

EP Opposition Response, "Auxiliary Request 2," in EP Appln No. 14815174.9, from response dated Jun. 25, 2021, 10 pages.

EP Opposition Response, "Auxiliary Request 3—marked up," in EP Appln No. 14815174.9, from response dated Jun. 25, 2021, 10 pages.

EP Opposition Response, "Auxiliary Request 3," in EP Appln No. 14815174.9, from response dated Jun. 25, 2021, 9 pages.

EP Opposition Response, "Auxiliary Request 4—marked up," in EP Appln No. 14815174.9, from response dated Jun. 25, 2021, 10 pages.

EP Opposition Response, "Auxiliary Request 4," in EP Appln No. 14815174.9, from response dated Jun. 25, 2021, 9 pages.

EP Opposition Response, "Auxiliary Request 5—marked up," in EP Appln No. 14815174.9, from response dated Jun. 25, 2021, 11 pages.

EP Opposition Response, "Auxiliary Request 5," in EP Appln No. 14815174.9, from response dated Jun. 25, 2021, 7 pages.

EP Opposition Response, "Data testing herbicidal activity of compounds IC1*, IC3* and IC6 against plants," Exhibit D16 in EP Appln. No. 14815174.9, from response dated Jun. 25, 2021, 5 pages.

(56) References Cited

OTHER PUBLICATIONS

EP Opposition Response, "Experimental data for further compounds," Exhibit D19 in EP Appln. No. 14815174.9, from response dated Jun. 25, 2021, 9 pages.
EP Opposition Response, "HRAC Mode of Action Classification 2021," Exhibit D21 in EP Appln. No. 14815174.9, from response dated Jun. 25, 2021, 2 pages.
EP Opposition Response, "Press Release—Novel herbicide tetflupyrolimet from FMC Corporation granted a new mode of action classification," Exhibit D20 in EP Appln. No. 14815174.9, dated Apr. 8, 2021, 3 pages.
EP Opposition Response, "Submission in Opposition Proceedings—FMC," in EP Appln. No. 14815174.9, dated Jun. 25, 2021, 43 pages.
EP Opposition, "Cudney—Why Herbicides Are Selective," Exhibit D22 in EP Appln. No. 14815174.9, 1996 Symposium Proceedings, 3 pages.
EP Opposition, "Notice of Opposition to a European Patent," in EP Appln. No. 14815174.9, dated Aug. 31, 2020, 55 pages.
EP Opposition, "English translation of the second amendments based on granted claims in CNIPA Decision," Exhibit D28 in EP Appln. No. 14815174.9, dated Apr. 15, 2021, 3 pages.
EP Opposition, "Smith—Organic Chemistry, an Acid-Base Approach," Exhibit D25 in EP Appln. No. 14815174.9, CRC Press, Taylor & Francis Group, LLC, 2011, pp. 24-32, 23 pages.
EP Opposition, "Submission In Opposition Proceedings—Syngenta," in EP Appln. No. 14815174.9, dated Nov. 5, 2020, 68 pages.
EP Opposition, "Summons to Attend Oral Proceedings Pursuant to Rule 115(1) EPC," in EP Appln. No. 14815174.9, dated Jul. 16, 2021, 14 pages.
EP Opposition, "TechLine Invasive Plant News—Factors Affecting Herbicide Performance," Exhibit D23 in EP Appln. No. 14815174.9, dated Jun. 2019, 9 pages.
EP Opposition, "US-PTAB Decision in relation to U.S. Pat. No. 10,294,202 B2," Exhibit D30 in EP Appln. No. 14815174.9, dated Aug. 31, 2021, 66 pages.
EP Opposition, "Walsh—Enzymatic Reaction Mechanisms," Exhibit D26 in EP Appln. No. 14815174.9, W. H. Freeman and Company, 1979, Chapter 2, pp. 24-48, 27 pages.
EP Opposition, "Williams—Opportunities for Chiral Agrochemicals," Exhibit D24 in EP Appln. No. 14815174.9, Pestic. Sci., 1996, 46:3-9.
EP Opposition, "Written Submission," in EP Appln. No. 14815174.9, dated Dec. 14, 2021, 3 pages.
EP Opposition, "Written Submission," in EP Appln. No. 14815174.9, dated Dec. 7, 2021, 2 pages.
EP Opposition, "Written Submission," in EP Appln. No. 14815174.9, dated Nov. 25, 2021, 32 pages.
EP Opposition, "Written Submission," in EP Appln. No. 14815174.9, dated Nov. 30, 2021, 6 pages.
IN Opposition, "Declaration of Dhaval Dayabhai Diyora," in IN Appln. No. 201617018886, dated Jun. 1, 2016, 60 pages.

* cited by examiner

HERBICIDAL MIXTURE, COMPOSITION AND METHOD

FIELD OF THE INVENTION

This invention relates to a mixture of certain substituted pyrrolidinone compounds and salts thereof, with florpyrauxifen-benzyl, compositions containing them, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. Many products are commercially available for these purposes, but the need continues for new mixtures, compositions and their method of use that are more effective, less costly, less toxic, environmentally safer or have different sites of action.

Combinations of herbicides are typically used to broaden the spectrum of plant control or enhance the level of control of any given species through additive effect. Certain rare combinations surprisingly give a greater-than-additive effect. Such valuable mixtures, compositions and methods have now been discovered.

WO 2015/084796 and WO 2016/196593 disclose a variety of substituted cyclic amides, methods of their use as herbicides, and methods to prepare them. The herbicide mixture, composition and method of the present invention are not disclosed in these publications.

SUMMARY OF THE INVENTION

This invention is directed to a mixture comprising (a) a compound of Formula I and salts thereof

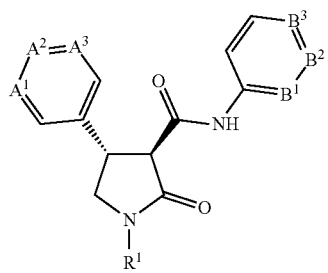

I wherein
$A^1$ is $CCF_3$, $A^2$ is CH and $A^3$ is CH; or
$A^1$ is CH, $A^2$ is $CCF_3$ and $A^3$ is CH; or
$A^1$ is N, $A^2$ is $CCF_3$ and $A^3$ is CH; or
$A^1$ is $CCH_3$, $A^2$ is N and $A^3$ is $COCHF_2$;
$R^1$ is $C_1$-$C_4$ alkyl;
$B^1$ is CF, $B^2$ is CH and $B^3$ is CH; or
$B^1$ is CF, $B^2$ is CF and $B^3$ is CH; or
$B^1$ is CF, $B^2$ is N and $B^3$ is CF;
and (b) 2-pyridinecarboxylic acid, 4-amino-3-chloro-6-(4-chloro-2-fluoro-3-methoxyphenyl)-5-fluoro-, phenylmethyl ester (i.e. florpyrauxifen-benzyl) and salts thereof.

This invention also includes the herbicidal mixture further comprising (c) at least one additional active ingredient.

This invention also relates to a herbicidal composition comprising a mixture of the invention (i.e. in a herbicidally effective amount) and at least one component selected from the group consisting of surfactants, solid diluents and liquid diluents.

This invention further relates to a method for controlling the growth of undesired vegetation comprising contacting the vegetation or its environment with a herbicidally effective amount of a mixture of the invention (e.g., as a composition described herein).

DETAILS OF THE INVENTION

As used herein, the terms "comprises," "comprising," "includes," "including," "has," "having," "contains," "containing," "characterized by" or any other variation thereof, are intended to cover a non-exclusive inclusion, subject to any limitation explicitly indicated. For example, a mixture, composition or method that comprises a list of elements is not necessarily limited to only those elements but may include other elements not expressly listed or inherent to such mixture, composition or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a mixture, composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed. As referred to herein, the term "broadleaf" used either alone or in words such as "broadleaf weed" means dicot or dicotyledon, a term used to describe a group of angiosperms characterized by embryos having two cotyledons.

In the above recitations, the term "alkyl" includes straight-chain or branched alkyl, such as, methyl, ethyl, n-propyl, i-propyl, or the different butyl isomers. In the compound of Formula I, the ring containing variables $A^1$, $A^2$ and $A^3$ can be represented by the following structures shown in Exhibit 1 where the bond projecting to the right indicates the attachment point to the remainder of Formula I.

Exhibit 1

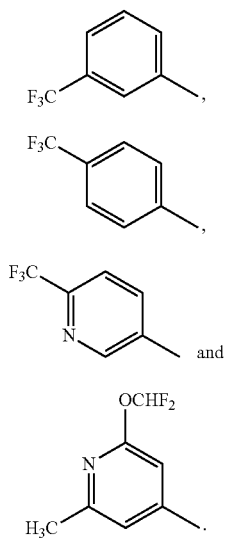

A-1

A-2

A-3

A-4

In the compound of Formula I, the ring containing variables $B^1$, $B^2$ and $B^3$ can be represented by the following structures shown in Exhibit 2 where the bond projecting to the left indicates the attachment point to the remainder of Formula I.

Exhibit 2

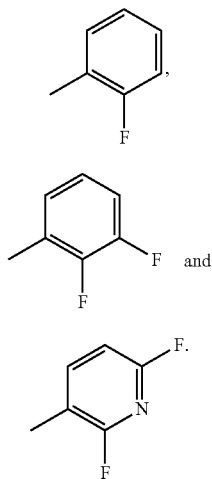

B-1

B-2

B-3

The total number of carbon atoms in a substituent group is indicated by the "$C_i$-$C_j$" prefix where i and j are numbers from 1 to 4. For example, $C_1$-$C_4$ alkyl designates methyl through butyl including the various isomers of an alkyl group.

The compound of Formula I of this invention can be prepared using the procedures outlined in U.S. application Ser. No. 15/101,615 (WO 2015/084796) and PCT/US2016/035214 (WO 2016/196593) both incorporated by reference.

The compound of Formula I of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compound of Formula I may be present as a mixture of stereoisomers, individual stereoisomers or as an optically active form. A compound of Formula I of this invention can exist as one or more conformational isomers due to restricted rotation about the amide bond (e.g., —C(=O)—NH—) in Formula I. This invention comprises mixtures of conformational isomers. In addition, this invention includes a compound of Formula I that is enriched in one conformer relative to others.

For example the C=O(NH) moiety (bonded to the carbon at the 3-position of the pyrrolidinone ring) and the ring containing the variables $A^1$, $A^2$ and $A^3$ (bonded to the carbon at the 4-position of the pyrrolidinone ring) are generally found in the trans configuration. Each of these two carbon atoms possesses a chiral center. The two most prevalent pairs of enantiomers are depicted as Formula I' and Formula I" below where the chiral centers are identified (i.e. as 3S,4S or as 3R,4R). While this invention pertains to all stereoisomers, the preferred enantiomeric pair for biological operability is identified as Formula I' (i.e. the 3S,4S configuration), and preferably the trans configuration. For a comprehensive discussion of all aspects of stereoisomerism, see Ernest L. Eliel and Samuel H. Wilen, *Stereochemistry of Organic Compounds*, John Wiley & Sons, 1994.

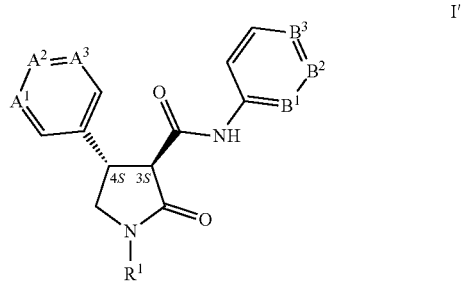

I'

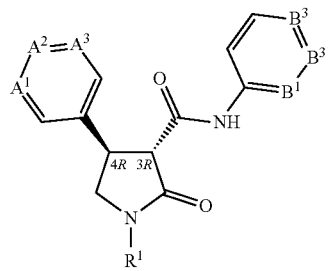

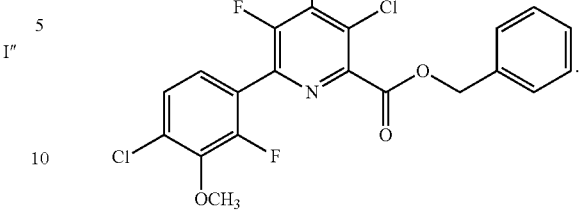

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the broad end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention comprises racemic mixtures, for example, equal amounts of the enantiomers of Formulae I' and I". In addition, this invention includes a compound of Formula I that is enriched compared to the racemic mixture in an enantiomer of a compound of Formula I. Also included are the essentially pure enantiomers of the compound of Formula I, for example, Formula I' and Formula I".

When enantiomerically enriched, one enantiomer is present in greater amounts than the other, and the extent of enrichment can be defined by an expression of enantiomeric excess ("ee"), which is defined as (2x−1) 100%, where x is the mole fraction of the dominant enantiomer in the mixture (e.g., an ee of 20% corresponds to a 60:40 ratio of enantiomers).

Preferably the compositions of this invention have at least a 50% enantiomeric excess; more preferably at least a 75% enantiomeric excess; still more preferably at least a 90% enantiomeric excess; and most preferably at least a 94% enantiomeric excess of the more active isomer. Of particular note are enantiomerically pure embodiments of the more active isomer.

Component (b) of the present invention is florpyrauxifen-benzyl (e.g., the compound of Formula II; 2-pyridinecarboxylic acid, 4-amino-3-chloro-6-(4-chloro-2-fluoro-3-methoxyphenyl)-5-fluoro-, phenylmethyl ester with CAS Registry No. 1390661-72-9) which comprises florpyrauxifen (containing an acid functional group (—CO$_2$H)) esterified with a benzyl moiety (i.e. —CH$_2$C$_6$H$_5$);

Although pictured with a benzyl moiety, embodiments of the compound of Formula II include replacement of benzyl with a hydrogen or C$_1$-C$_4$ alkyl moiety, resulting in the acid or C$_1$-C$_4$ alkyl ester. Florpyrauxifen-benzyl is commercially available as, for example, Loyant™ herbicide with Rinskor™ active (Dow AgroSciences). For the present recitations, the compound of Formula II was prepared according to the methods described in WO 2010/125332 A1 and Org. Let. 2015, 17, 2905 with a melting point of 138-142° C. Alternatively, florpyrauxifen (i.e. the acid) can be prepared according to the methods described in U.S. Pat. No. 7,314,849 (B2) which is incorporated by reference, or purchased in research quantities. Florpyrauxifen-benzyl contains a nitrogen atom with a free pair of electrons capable of protonation and forming salts with acids. Particularly useful for the present mixture, composition and method are salts formed with bases. Florpyrauxifen-benzyl is known to mimic the plant growth hormone auxin, thus causing uncontrolled and disorganized growth leading to plant death in susceptible species ("auxin mimic"). In the present disclosure and claims, the molecular weight of florpyrauxifen-benzyl is calculated as 439.2 g/mole.

The compounds of Formulae I and II can exist in more than one form, and thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of compounds of Formulae I and II can exhibit beneficial effects (e.g., suitability for preparation of useful formulations, improved biological performance) relative to another polymorph or a mixture of polymorphs of the same compounds of Formulae I and II. Preparation and isolation of a particular polymorph of compounds of Formulae I and II can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art recognizes that because in the environment and under physiological conditions salts of chemical compounds are in equilibrium with their corresponding nonsalt forms, salts share the biological utility of the nonsalt forms. Thus a wide variety of salts of compounds of Formulae I and II are useful for control of undesired vegetation (i.e. are agriculturally suitable). The salts of compounds of Formulae I and II include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Embodiments of the present invention as described in the Summary of the Invention include the following where Formula I as used in the following Embodiments includes salts thereof:

Embodiment 1

The mixture as described in the Summary of the Invention wherein $A^1$ is $CCF_3$, $A^2$ is CH and $A^3$ is CH.

Embodiment 2

The mixture as described in the Summary of the Invention wherein $A^1$ is CH, $A^2$ is $CCF_3$ and $A^3$ is CH.

Embodiment 3

The mixture as described in the Summary of the Invention wherein $A^1$ is N, $A^2$ is $CCF_3$ and $A^3$ is CH.

Embodiment 4

The mixture as described in the Summary of the Invention wherein $A^1$ is $CCH_3$, $A^2$ is N and $A^3$ is $COCHF_2$.

Embodiment 5

The mixture of any one of Embodiments 1 through 4 wherein $R^1$ is methyl, ethyl or propyl.

Embodiment 6

The mixture of Embodiment 5 wherein $R^1$ is methyl or ethyl.

Embodiment 7

The mixture of Embodiment 6 wherein $R^1$ is methyl.

Embodiment 8

The mixture of any one of Embodiments 1 through 7 wherein $B^1$ is CF, $B^2$ is CH and $B^3$ is CH.

Embodiment 9

The mixture of any one of Embodiments 1 through 7 wherein $B^1$ is CF, $B^2$ is CF and $B^3$ is CH.

Embodiment 10

The mixture of any one of Embodiments 1 through 7 wherein $B^1$ is CF, $B^2$ is N and $B^3$ is CF.

Embodiment 11

The mixture of any one of Embodiments 5 through 7 wherein when $A^1$ is $CCF_3$, $A^2$ is CH and $A^3$ is CH, then $B^1$ is CF, $B^2$ is CH and $B^3$ is CH (Compound 1).

Embodiment 12

The mixture of any one of Embodiments 5 through 7 wherein when $A^1$ is $CCF_3$, $A^2$ is CH and $A^3$ is CH, then $B^1$ is CF, $B^2$ is N and $B^3$ is CF (Compound 2).

Embodiment 13

The mixture of any one of Embodiments 5 through 7 wherein when $A^1$ is N, $A^2$ is $CCF_3$ and $A^3$ is CH, then $B^1$ is CF, $B^2$ is CF and $B^3$ is CH (Compound 3).

Embodiment 14

The mixture of any one of Embodiments 5 through 7 wherein when $A^1$ is $CH_3$, $A^2$ is N and $A^3$ is $COCHF_2$, then $B^1$ is CF, $B^2$ is CF and $B^3$ is CH (Compound 4).

Embodiment 15

The mixture of any one of Embodiments 5 through 7 wherein when $A^1$ is CH, $A^2$ is $CCF_3$ and $A^3$ is CH, then $B^1$ is CF, $B^2$ is CF and $B^3$ is CH (Compound 5).

Embodiment 16

The mixture of any one of Embodiments 5 through 7 wherein when $A^1$ is CH, $A^2$ is $CCF_3$ and $A^3$ is CH, then $B^1$ is CF, $B^2$ is N and $B^3$ is CF (Compound 6).

Embodiment 17

The mixture as described in the Summary of the Invention or any one of Embodiments 1 through 16 wherein the weight ratio of (a) to (b) is from about 1:20 to about 56:1.

Embodiment 18

The mixture as described in the Summary of the Invention or any one of Embodiments 1 through 16 wherein the weight ratio of (a) to (b) is from about 1:6 to about 19:1.

Embodiment 19

The mixture as described in the Summary of the Invention or any one of Embodiments 1 through 16 wherein the weight ratio of (a) to (b) is from about 1:2 to about 4:1.

Embodiment 20

The mixture as described in the Summary of the Invention or any one of Embodiments 1 through 16 wherein the weight ratio of (a) to (b) is from about 100:1 to about 4:1.

Embodiment 21

The mixture as described in the Summary of the Invention or any one of Embodiments 1 through 16 wherein the weight ratio of (a) to (b) is from about 75:1 to about 5:1.

Embodiment 22

The mixture as described in the Summary of the Invention or any one of Embodiments 1 through 16 wherein the weight ratio of (a) to (b) is about 50:1 to about 10:1.

Embodiment 23

The mixture as described in the Summary of the Invention or any one of Embodiments 1 through 16 wherein the weight ratio of (a) to (b) is about 40:1 to about 10:1.

Embodiment 24

The mixture as described in the Summary of the Invention or any one of Embodiments 1 through 16 wherein the weight ratio of (a) to (b) is 37.5:1 to 12.5:1.

Embodiment 25

The mixture as described in the Summary of the Invention or any one of Embodiments 1 through 16 wherein the weight ratio of (a) to (b) is 25:1 to 12.5:1.

Embodiment 26

The mixture as described in the Summary of the Invention or any one of Embodiments 1 through 16 wherein the weight ratio of (a) to (b) is 18.75:1 to 12.5:1.

Embodiment 27

The mixture as described in the Summary of the Invention or any one of Embodiments 1 through 16 wherein the weight ratio of (a) to (b) is 25:1 to 18.75:1.

Embodiment 28

The mixture as described in the Summary of the Invention or any one of Embodiments 1 through 27 wherein the mixture is formulated with solid or liquid diluents.

Embodiment 29

The mixture of Embodiment 28 formulated as a solid soluble granule.

Embodiment 30

The mixture of any one of Embodiments 1 through 29 wherein the mixture controls the growth of grass weeds.

Embodiment 31

The mixture of any one of Embodiments 1 through 29 wherein the mixture controls the growth of broadleaf weeds.

Embodiment 32

The mixture of any one of Embodiments 1 through 29 wherein the mixture controls the growth of sedge weeds.

Embodiment 33

The mixture of any one of Embodiments 1 through 29 wherein the mixture controls the growth of weeds from the genus selected from the group consisting of *Cyperus*, *Echinochloa*, *Heteranthera*, *Leptochloa* and *Monochoria*.

Embodiment 34

The mixture of Embodiment 33 wherein the mixture controls the growth of weeds from the genus *Cyperus*.

Embodiment 35

The mixture of Embodiment 34 wherein the species is *difformis*.

Embodiment 36

The mixture of Embodiment 33 that controls the growth of weeds from the genus selected from the group consisting *Echinochloa* and *Leptochloa*.

Embodiment 37

The mixture of Embodiment 36 that controls the growth of weeds from the genus *Echinochloa*.

Embodiment 38

The mixture of Embodiment 37 wherein the species is *chinensis*.

Embodiment 39

The mixture of Embodiment 37 wherein the species is *phyllopogon*.

Embodiment 40

The mixture of Embodiment 33 that controls the growth of weeds from the genus *Leptochloa*.

Embodiment 41

The mixture of Embodiment 40 wherein the species is *chinensis*.

Embodiment 42

The mixture of Embodiment 33 that controls the growth of weeds from the genus selected from the group consisting *Heteranthera* or *Monochoria*.

Embodiment 43

The mixture of Embodiment 42 that controls the growth of weeds from the genus *Heteranthera*.

Embodiment 44

The mixture of Embodiment 43 wherein the species is *limosa*.

Embodiment 45

The mixture of Embodiment 42 that controls the growth of weeds from the genus *Monochoria*.

Embodiment 46

The mixture of Embodiment 45 wherein the species is *vaginalis*.

Embodiment 47

The mixture of any one of Embodiments 30 through 46 wherein the weeds are growing in japonica rice (*Oyrza sativa*).

Embodiments of this invention, including Embodiments 1-47 above as well as any other embodiments described herein, and any combination thereof, pertain to the compositions and methods of the present invention.

Combinations of Embodiments 1-47 are illustrated by:

Embodiment A

The mixture of the Summary of the Invention wherein $R^1$ is methyl, ethyl or propyl.

Embodiment B

The mixture of the Summary of the Invention wherein $R^1$ is methyl.

Embodiment C

The mixture of the Summary of the Invention wherein the weight ratio of (a) to (b) is from about 1:20 to about 56:1.

Embodiment D

The mixture of the Summary of the Invention wherein the mixture controls the growth of weeds from the genus selected from the group consisting *Cyperus. Echinochloa, Heteranthera, Leptochloa* and *Monochoria*.

Embodiment E

The mixture of Embodiment D wherein the mixture controls the growth of weeds from the growth from the genus *Cyperus*.

Embodiment F

The mixture of Embodiment E wherein the species is *difformis*.

Embodiment G

The mixture of Summary of the Invention or any one of Embodiments A through F wherein the weeds are growing in *Oryza sativa*.

The mixture of this invention further comprising (c) at least one additional active ingredient includes herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the invention with other herbicides can broaden the spectrum of activity against additional weed species, and suppress the proliferation of any resistant biotypes. Thus the present invention also pertains to a composition further comprising at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a present mixture, to form a premix, or one or more other biologically active compounds or agents can be formulated separately from the compound of Formula I, and the formulations combined together before application (e.g., in a spray tank) or, alternatively, applied in succession.

Appropriate as the one additional active ingredient, (i.e. as component (c)) at least one additional active ingredient can be one or more of the following herbicides particularly useful for weed control: acetochlor, acifluorfen and its sodium salt, aclonifen, acrolein (2-propenal), alachlor, alioxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuronethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimetharnetryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuronmethyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-benzyl, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, tricopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy] methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfin 4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Preferred for better control of undesired vegetation (e.g., lower use rate such as from greater-than-additive effects, broader spectrum of weeds controlled, or enhanced crop safety) or for preventing the development of resistant weeds are mixtures of a compound of this invention with a herbicide selected from the group consisting of atrazine, azimsulfuron, beflubutamid, benzisothiazolinone, carfentrazone-ethyl, chlorimuron-ethyl, chlorsulfuron-methyl, clomazone, clopyralid potassium, cloransulam-methyl, ethametsulfuron-methyl, flumetsulam, 4-(4-fluorophenyl)-6-[(2-hydroxy-6-oxo-1-cyclohexen-1-yl)carbonyl]-2-methyl-1,2,4-triazine-3,5-(2H,4H)-dione, flupyrsulfuron-methyl, fluthiacet-methyl, fomesafen, imazethapyr, lenacil, mesotrione, metribuzin, metsulfuron-methyl, pethoxamid, picloram, pyroxasulfone, quinclorac, rimsulfuron, S-metolachlor, sulfentrazone, thifensulfuron-methyl, triflusulfuron-methyl and tribenuron-methyl.

Mixtures of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th *Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the present mixture is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the present mixture alone.

In certain instances, combinations of a mixture of this invention with other biologically active (particularly herbicidal) compounds or agents (i.e. active ingredients) can result in a greater-than-additive effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When greater-than-additive effects of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a mixture of the invention with at least one other herbicidal active ingredient (i.e. as component (c)). Of particular note is such a combination where the other herbicidal active ingredient has different site of action from either component (a) or component (b) of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

The mixtures of this invention can also be used in combination with herbicide safeners (i.e. as component (c)) selected from allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimnidinecarboxylate, 2,2-dichloro-1-(2,2,5-trimethyl-3-ox azolidinyl)-ethanone and 2-methoxy-1-[[4-[[[(methylamino)carbonyl]amino]phenyl]sulfonyl]-benzamide to increase safety to certain crops. Antidotally effective amounts of the herbicide safeners can be applied at the same time as the mixtures of this invention, or applied as seed treatments. Therefore an aspect of the present invention relates to a herbicidal mixture comprising a mixture of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a mixture of this invention wherein seed from which the crop is grown is treated with an antidotally effective amount of safener. Antidotally effective amounts of safeners can be easily determined by one skilled in the art through simple experimentation.

This invention also relates to a method for controlling undesired vegetation comprising applying to the locus of the vegetation herbicidally effective amounts of the mixture of the invention (e.g., as a composition described herein). Of note as embodiments relating to methods of use are those involving the mixtures of embodiments described above. Mixtures of the invention are particularly useful for selective control of weeds in crops such as wheat, barley, maize, soybean, sunflower, cotton, oilseed rape and rice, and specialty crops such as sugarcane, citrus, fruit and nut crops. Of note of the present invention is the selective control of weeds in a transplanted rice crop. Also of note is the selective control of weeds in a direct-seeded rice crop.

A mixture of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient as a mixture | Diluent | Surfactant |
| Water-Dispersible and Water-soluble Granules, Tablets and Powders | 0.001-90 | 0-99.999 | 0-15 |

|  | Weight Percent | | |
| --- | --- | --- | --- |
|  | Active Ingredient as a mixture | Diluent | Surfactant |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, New Jersey.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_2$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents*, Chemical Publ. Co., Inc., New York, 1964: and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The mixtures of a compound of Formula I and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry* and *Bioscience. The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; I-lance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Cmpd. No. 1 and florpyrauxifen-benzyl | 98.5% |
| silica aerogel | 0.5% |
| synthetic amorphous fine silica | 1.0% |

Example B

| Wettable Powder | |
|---|---|
| Cmpd. No. 1 and florpyrauxifen-benzyl | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Cmpd. No. 1 and florpyrauxifen-benzyl | 10.0% |
| attapulgite granules (low volatile matter, 0.71/0.30 mm; U.S.S. No. 25-50 sieves) | 90.0% |

Example D

| Extruded Pellet | |
|---|---|
| Cmpd. No. 1 and florpyrauxifen-benzyl | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Cmpd. No. 1 and florpyrauxifen-benzyl | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Cmpd. No. 1 and florpyrauxifen-benzyl | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Suspension Concentrate | |
|---|---|
| Cmpd. No. 1 and florpyrauxifen-benzyl | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

| Emulsion in Water | |
|---|---|
| Cmpd. No. 1 and florpyrauxifen-benzyl | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

| Oil Dispersion | |
|---|---|
| Cmpd. No. 1 and florpyrauxifen-benzyl | 25% |
| polyoxyethylene sorbitol hexaoleate | 15% |
| organically modified bentonite clay | 2.5% |
| fatty acid methyl ester | 57.5% |

The present disclosure also includes Examples A through I above except that "Cmpd. No. 1" is replaced with "Cmpd. No. 2", "Cmpd. No. 3", "Cmpd. No. 4". "Cmpd. No. 5" and "Cmpd. No. 6".

Test results indicate that the mixtures of the present invention are highly active preemergent and/or postemergent herbicides and/or plant growth regulants. The mixtures of the present invention generally show highest activity for postemergence weed control (i.e. applied after weed seedlings emerge from the soil) and preemergence weed control (i.e. applied before weed seedlings emerge from the soil). Many of the mixtures of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors can readily be determined by performing routine biological and/or biochemical assays. Mixtures of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Of note is a rice crop that is direct-seeded. Of note is a rice crop that transplanted. Mixtures of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all mixtures are equally effective against all weeds. Alternatively, the subject mixtures are useful to modify plant growth.

As the mixture of the invention have both preemergent and postemergent herbicidal activity, to control undesired vegetation by killing or injuring the vegetation or reducing its growth, the mixture can be usefully applied by a variety of methods involving contacting a herbicidally effective amount of a mixture of the invention, or a composition comprising said mixture and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the mixtures of this invention is determined by a number of factors. These factors include: formulation selected, method of application, amount and type of vegetation present, growing conditions, etc. In general, a herbicidally effective amount of mixtures of this invention is about 0.001 to 20 kg/ha with a preferred range of about 0.004 to 1 kg/ha, about 0.004 to 0.5 kg/ha, about 0.004 to 0.25 kg/ha, about 0.004 to 0.1 kg/ha, 0004 to 0.075 kg/ha or 0.004 to 0.05 kg/ha. One skilled in the art can determine the herbicidally effective amount necessary for the desired level of weed control.

In one common embodiment, a mixture of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a mixture of the invention can be directly applied to a plant or a part thereof, particularly of the undesired vegetation, and/or to the growth medium in contact with the plant.

Plant varieties and cultivars of the desired vegetation in the locus treated with a mixture of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The herbicidal mixture can be formulated as single, separate ingredients (i.e as a co-pack) and mixed together (i.e. as a tank mix). Alternatively, the herbicidal mixture can be formulated separately, then mixed together before adding to the spray tank (i.e. a homogenous blend of soluble granules). Alternatively, the herbicidal mixture can be formulated together, then formulated, (i.e. as soluble granules). The amount of each compound of the herbicidal mixture (i.e. as component (a) and (b) (and optionally (c)) can be adjusted according to field conditions present. Likewise, the method of applying the herbicidal mixture or composition also comprises the sequential application of component (a) followed by component (b), or in reverse order.

Of note is a composition comprising a mixture of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

The following Tests demonstrate the control efficacy of the mixture of this invention against specific weeds. The weed control afforded by the mixture is not limited, however, to these species. See Index Table A for compound descriptions. The abbreviation "Cmpd. No." stands for "Compound Number".

INDEX TABLE A

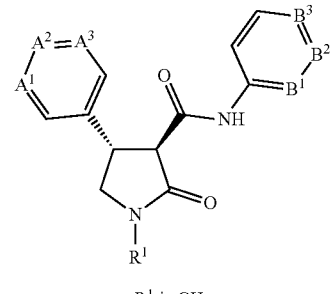

$R^1$ is $CH_3$

| Cmpd. No. | | M.P. °C. |
|---|---|---|
| 1 | $A^1$ is $CCF_3$, $A^2$ is CH, $A^3$ is CH, $B^1$ is CF, $B^2$ is CH and $B^3$ is CH | 141.2-142.3 |
| 2 | $A^1$ is $CCF_3$, $A^2$ is CH, $A^3$ is CH, $B^1$ is CF, $B^2$ is N and $B^3$ is CF | 139-140 |
| 3 | $A^1$ is N, $A^2$ is $CCF_3$, $A^3$ is CH, $B^1$ is CF, $B^2$ is CF and $B^3$ is CH | * |
| 4 | $A^1$ is $CCH_3$, $A^2$ is N, $A^3$ is $COCHF_2$, $B^1$ is CF, $B^2$ is CF and $B^3$ is CH | * |
| 5 | $A^1$ is CH, $A^2$ is $CCF_3$, $A^3$ is CH, $B^1$ is CF, $B^2$ is CF and $B^3$ is CH | 164-165.7 |
| 6 | $A^1$ is CH, $A^2$ is $CCF_3$, $A^3$ is CH, $B^1$ is CF, $B^2$ is N and $B^3$ is CF | * |

* See Index Table B for $^1$H NMR data.

INDEX TABLE B

| Cmpd. No. | $^1$H NMR Data (CDCl$_3$ solution unless indicated otherwise)$^a$ |
|---|---|
| 3 | δ 3.04 (s, 3H), 3.53 (dd, 1H), 3.64 (d, 1H), 3.83 (dd, 1H), 4.19 (q, 1H), 6.87-6.93 (m, 1H), 7.00-7.05 (m, 1H), 7.71 (d, 1H), 7.90 (d, 1H), 7.95 (t, 1H), 8.79 (s, 1H), 10.0 (s, 1H). |
| 4 | δ 2.48 (s, 3H), 3.01 (s, 3H), 3.43 (dd, 1H), 3.62 (d, 1H), 3.78 (dd, 1H), 4.06 (dd, 1H), 6.69 (s, 1H), 6.88-6.93 (m, 1H), 6.95 (s, 1H), 7.01-7.05 (m, 1H), 7.51 (t, 1H), 7.97-8.01 (m, 1H), 10.03 (s, 1H). |
| 6 | δ 3.02 (s, 3H), 3.48 (dd, 1H), 3.64 (d, 1H), 3.81 (dd, 1H), 4.12 (q, 1H), 6.78 (dd, 1H), 7.49 (d, 2H), 7.65 (d, 2H), 8.72 (m, 1H), 10.07 (s, 1H). |

$^a$$^1$H NMR data are in ppm downfield from tetramethylsilane.
Couplings are designated by (s)—singlet, (d)—doublet, (t)—triplet, (m)—multiplet, (q)—quartet, (dd)—doublet of doublets.

Biological Examples of the Invention

Test A

Seeds of Asian sprangletop (LEPCH, *Leptochloa chinensis*), smallflower umbrella sedge (CYPDI, *Cyperus difformis*), monochoria (MOOVA, *Monochoria vaginalis*) and ducksalad (HETLI, *Heteranthera limosa*) were sown on the soil surface in four separate quadrants of 16-cm tubs filled with steam pasteurized Tama soil. Simultaneously, plantings of barnyardgrass (ECHCG, *Echinochloa crus-galli*), japonica rice (ORYSA, *Oryza sativa*) and late watergrass (ECHPH, *Echinochloa phyllopogon*) were established in separate "plug" flats. Plants were grown in a greenhouse using supplemental lighting to maintain a photoperiod of approximately 16 h; daytime and nighttime temperatures were approximately 27-30° C. and 24-27° C., respectively.

After 8 d, barnyardgrass, rice and late watergrass plants were transplanted in 3 quadrants of separate tub, and the water level was adjusted to a final depth of 3 cm. Herbicide application of Cmpd. No. 1 and florpyrauxifen-benzyl (CAS Registry No. 1390661-72-9; 439.2 g/mol) timing was targeted at the 2.0 to 2.5 leaf stage and the plants were treated with test chemicals formulated in a non-phytotoxic solvent. Treated plants and controls were maintained in a greenhouse for 14 d, after which time all species were compared to controls and visually evaluated. Plant response ratings are summarized in Table A, and are based on a scale of 0 to 100 where 0 is no effect and 100 is complete control and is the mean of duplicate ratings. A dash (-) response means no test result.

Colby's Equation was used to determine the herbicidal effects expected from the mixtures. Colby's Equation (Colby, S. R. "Calculating Synergistic and Antagonistic Responses of Herbicide Combinations," *Weeds* 1967 15(1), pp 20-22) calculates the expected additive effect of herbicidal mixtures and for two active ingredients is of the form:

$$P_{a+b} = P_a + P_b - (P_a P_b / 100)$$

wherein $P_{a+b}$ is the percentage effect of the mixture expected from additive contribution of the individual components:

$P_a$ is the observed percentage effect of the first active ingredient at the same use rate as in the mixture, and $P_b$ is the observed percentage effect of the second active ingredient at the same use rate as in the mixture.

The results and additive effects expected from Colby's Equation are listed in Table A. Application rates are grams of active ingredient per hectare (g a.i./ha). "Obsd." is the observed effect and "Exp." is expected effect calculated from Colby's Equation.

TABLE A

Observed and Expected Results from Compound 1 Alone and in Combination with Florpyrauxifen-benzyl (CAS Registry No. 1390661-72-9; 439.2 g/mol)

| Application Rate (g a.i./ha) | | Crop | | Grass Weeds | | | | | |
|---|---|---|---|---|---|---|---|---|---|
| Cmpd. No. 1 | florpyrauxifen-benzyl | ORYSA | | ECHCG | | ECHPH | | LEPCH | |
| | | Obsd. | Exp. | Obsd. | Exp. | Obsd. | Exp. | Obsd. | Exp. |
| 50 | — | 0 | — | 70 | — | 75 | — | 75 | — |
| 75 | — | 0 | — | 70 | — | 85 | — | 85 | — |
| — | 2 | 0 | — | 0 | — | 0 | — | 0 | — |
| — | 4 | 0 | — | 0 | — | 0 | — | 0 | — |
| 50 | 2 | 0 | 0 | 75 | 70 | 85 | 75 | 75 | 75 |
| 75 | 2 | 0 | 0 | 75 | 70 | 90 | 85 | 90 | 85 |
| 50 | 4 | 0 | 0 | 75 | 70 | 80 | 75 | 75 | 75 |
| 75 | 4 | 0 | 0 | 75 | 70 | 90 | 85 | 85 | 85 |

| Application Rate (g a.i./ha) | | Broadleaf Weeds | | | | Sedge | |
|---|---|---|---|---|---|---|---|
| Cmpd. No. 1 | florpyrauxifen-benzyl | MOOVA | | HETLI | | CYPDI | |
| | | Obsd. | Exp. | Obsd. | Exp. | Obsd. | Exp. |
| 50 | — | 70 | — | 70 | — | 0 | — |
| 75 | — | 70 | — | 70 | — | 0 | — |
| — | 2 | 90 | — | 90 | — | 80 | — |
| — | 4 | 100 | — | 100 | — | 85 | — |
| 50 | 2 | 100 | 97 | 100 | 97 | 80 | 80 |
| 75 | 2 | 100 | 97 | 100 | 97 | 85 | 80 |
| 50 | 4 | 100 | 100 | 100 | 100 | 100 | 85 |
| 75 | 4 | 100 | 100 | 100 | 100 | 100 | 85 |

As can be seen from the results listed in Table A, all of the observed results for weed species were greater than the expected results from the Colby Equation, thereby showing the additive effect of Compound 1 and florpyrauxifen-benzyl on ECHCG and ECHPH. The observed results for weed species were greater than additive or equal to the expected results from the Colby Equation, thereby showing the additive or expected results on LEPCH and CYPDI. Also, excellent crop safety to rice was observed with the mixture, similar to when Compound 1 and florpyrauxifen-benzyl were applied separately.

Test B

Seeds of plant species selected from barnyardgrass (*Echinochloa crus-galli*), kochia (*Kochia scoparia*), ragweed (common ragweed, *Ambrosia elatior*), Ryegrass, Italian (Italian ryegrass, *Lolium multiflorum*), foxtail, green (green foxtail, *Setaria viridis*), and pigweed (*Amaranthus retroflexus*) were planted into a blend of loam soil and sand and treated preemergence with a directed soil spray using test chemicals formulated in a non-phytotoxic solvent mixture which included a surfactant.

At the same time, plants selected from these weed species and also wheat (*Triticum aestivum*), corn (*Zea mays*), blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table B, are based on a 0 to 100 scale where 0 is no effect and 100 is complete control. A dash (-) response means no test result.

TABLE B

| 125 g ai/ha | Cmpd. No. 4 | 31 g ai/ha | Cmpd. No. 4 |
|---|---|---|---|
| Postemergence | | | |
| Barnyardgrass | 90 | Barnyardgrass | 80 |
| Blackgrass | 70 | Blackgrass | 60 |
| Corn | 80 | Corn | 60 |
| Foxtail, Green | 90 | Foxtail, Green | 70 |
| *Galium* | 60 | *Galium* | 0 |
| *Kochia* | 20 | *Kochia* | 0 |
| Pigweed | 60 | Pigweed | 20 |
| Ragweed | 60 | Ragweed | 0 |
| Ryegrass, Italian | 70 | Ryegrass, Italian | 30 |
| Wheat | 70 | Wheat | 40 |
| Preemergence | | | |
| Barnyardgrass | 100 | Barnyardgrass | 100 |
| Foxtail, Green | 100 | Foxtail, Green | 100 |
| *Kochia* | 80 | *Kochia* | 0 |
| Pigweed | 90 | Pigweed | 40 |
| Ragweed | 20 | Ragweed | 0 |
| Ryegrass, Italian | 90 | Ryegrass, Italian | 30 |

Test C Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table C, are based on a scale of 0 to 100 where 0 is no effect and 100 is complete control. A dash (-) response means no test result.

TABLE C

| 250 g ai/ha | Cmpd. No. 4 |
|---|---|
| Flood | |
| Barnyardgrass | 85 |
| Ducksalad | 100 |
| Rice | 30 |
| Sedge, Umbrella | 0 |

What is claimed is:

1. A mixture comprising (a) a compound of Formula I and salts thereof

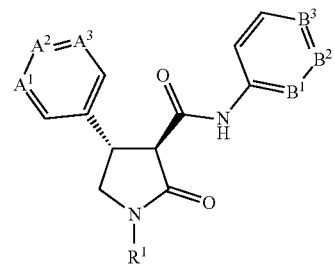

wherein
$A^1$ is $CCF_3$, $A^2$ is CH, $A^3$ is CH, $B^1$ is CF, $B^2$ is CH, $B^3$ is CH;
$R^1$ is methyl;
and (b) a compound of Formula II and salts thereof

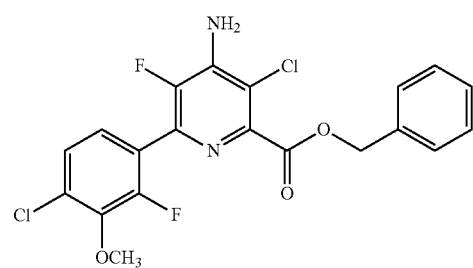

and wherein the weight ratio of (a) to (b) is 25:1 to 12.5:1.

2. The mixture of claim 1 wherein the mixture controls the growth of weeds from the genus selected from the group consisting *Cyperus, Echinochloa, Heteranthera, Leptochloa* and *Monochoria*.

3. The mixture of claim 2 wherein the mixture controls the growth of weeds from the genus *Cyperus*.

4. The mixture of claim 3 wherein the species is *difformis*.

5. The mixture of claim 2 wherein the weeds are growing in *Oryza sativa*.

6. The mixture of claim 1 further comprising (c) at least one additional active ingredient.

7. The mixture of claim 1 further comprising at least one component selected from the group consisting of surfactants, solid diluents and liquid diluents.

8. A method for controlling the growth of undesired vegetation comprising contacting the vegetation or its environment with a herbicidally effective amount of a mixture of claim 1.

* * * * *